United States Patent [19]

Shaw

[11] Patent Number: 5,232,623
[45] Date of Patent: Aug. 3, 1993

[54] CATALYST AND PROCESS FOR PRODUCING ORGANIC POLYSULFIDE

[75] Inventor: James E. Shaw, Bartlesville, Okla.

[73] Assignee: Phillips Petroleum Company, Bartlesville, Okla.

[21] Appl. No.: 929,746

[22] Filed: Aug. 17, 1992

[51] Int. Cl.$^5$ .............. C09K 3/00; C07C 321/00; C07C 323/00; C07C 381/00
[52] U.S. Cl. .............. 252/183.13; 252/182.3; 568/26
[58] Field of Search ............ 568/26; 252/188.13, 252/182.3

[56] References Cited

U.S. PATENT DOCUMENTS

| | | | |
|---|---|---|---|
| 3,022,351 | 2/1962 | Mihm et al. | 568/26 |
| 3,308,166 | 3/1967 | Biensan et al. | 568/26 |
| 4,279,806 | 7/1981 | Muldrow | 524/301 |
| 4,415,694 | 11/1983 | Roiko et al. | 524/200 |
| 4,745,162 | 5/1988 | Harris | 525/461 |
| 4,804,485 | 2/1989 | Carroll et al. | 252/8.552 |
| 4,868,336 | 9/1989 | Presnall | 568/25 |
| 4,870,127 | 9/1989 | Harris | 524/537 |
| 4,876,389 | 10/1989 | Gongora et al. | 568/26 |
| 4,933,481 | 6/1990 | Valee et al. | 568/26 |
| 4,937,385 | 6/1990 | Buchholz et al. | 568/26 |
| 5,001,269 | 3/1991 | Gongora et al. | 568/26 |
| 5,068,445 | 11/1991 | Arretz | 568/21 |
| 5,091,593 | 2/1992 | Lindstrom et al. | 568/21 |

OTHER PUBLICATIONS

Filed application Ser. No. 07/875,489 (Shaw, James E., Apr. 29, 1992).

*Primary Examiner*—Donald P. Walsh
*Assistant Examiner*—Anthony R. Chi
*Attorney, Agent, or Firm*—Lucas K. Shay

[57] ABSTRACT

A composition comprising a base and an alkoxylated compound selected from an alkoxylated alcohol and alkoxylated mercaptan is disclosed. The composition can be used to catalyze the reaction of a mercaptan and an elemental sulfur to produce a polysulfide compound. The polysulfide compound can be further treated with an alkylene oxide to reduce the mercaptan sulfur content of the polysulfide compound.

14 Claims, No Drawings

CATALYST AND PROCESS FOR PRODUCING ORGANIC POLYSULFIDE

FIELD OF THE INVENTION

The present invention relates to a catalyst composition and to a process using the composition for producing stable organic polysulfide compounds.

BACKGROUND OF THE INVENTION

Organic polysulfides are useful for many purposes such as additives for elastomers, antioxidants for lubricating oils, intermediates for the production of organic chemicals, insecticides, germicides and as an additive to diesel fuels to improve the cetane number and ignition qualities of these fuels. These compounds are also useful in the compounding of extreme pressure lubricants and in the acceleration of rubber treating processes.

Such polysulfide compounds can be prepared by reacting mercaptans with elemental sulfur in the presence of a basic catalyst. For example, Biesan et al (U.S. Pat. No. 3,308,166) discloses that polysulfides can be prepared from a mercaptan and sulfur catalyzed by an amine using an alcohol promoter.

A conventional process for producing a polysulfide compound such as di-t-dodecyl polysulfide is to react a mercaptan such as t-dodecyl mercaptan with elemental sulfur in the presence of triethylamine as catalyst. However, the polysulfide thus prepared is associated with as high as 19 weight % of unreacted mercaptans and residual $H_2S$ contributing to unpleasant odor and an unsatisfactory product. Additionally, high content of unreacted mercaptans indicates an incompletion of the reaction towards polysulfide. Further, possibly because of the unreacted mercaptans and the amine catalyst, the product always becomes very unstable, i.e. the product turns cloudy, probably due to degradation of the polysulfide causing precipitation of sulfur. These problems greatly reduce the desirability and utility of the polysulfide product.

Kamii et al (Japanese Applicant 58-140,063) discloses a process for deodorizing dialkyl polysulfides by contacting the polysulfide-bearing fluid with 1,2-epoxy compounds. The 1,2-epoxy compound apparently react directly with the unreacted mercaptan and hydrogen sulfide, thereby producing a product with reduced odor. Excess 1,2-epoxy compounds are reportedly removed by convention methods, such as vacuum distillation.

However, due to the high content of unreacted mercaptans, as described above, such treatment greatly reduces the yield of an organic polysulfide compound. Additionally, employing the process disclosed in Kamii et al produces a product that still has such high mercaptan level that it would contribute the instability of a polysulfide product. It would therefore be a significant contribution to the art to develop a catalyst and a process using the catalyst for producing a polysulfide product having substantially reduced unreacted mercaptans so that the product is stable and is made more useful for industrial uses.

SUMMARY OF THE INVENTION

An object of the present invention is to provide a catalyst composition that is useful in producing a stable polysulfide compound. Also an object of the present invention is to develop a process using the catalyst for producing an organic polysulfide. Another object of the present invention is to reduce the odor associated with the polysulfide compound. A further object of the present invention is to reduce unreacted or residual sulfur-containing compounds contaminating the polysulfide. Yet another object of the present invention is to prepare a polysulfide that is table and deodorized.

An advantage of the present invention is the reduction of the concentration of sulfur content of unreacted mercaptans to as low as 30 ppm while maintaining the polysulfide in high yield. Other advantages and features will become more apparent as the invention is more fully disclosed hereinbelow.

According to a first embodiment of the present invention, a composition useful for catalyzing the reaction of a mercaptan and elemental sulfur is provided which comprises a base and an alkoxylated compound selected from the group consisting of alkoxylated alcohol and alkoxylated mercaptan, and mixtures thereof.

According to a second embodiment of the present invention, a process for producing an organic polysulfide is provided which comprises contacting a mercaptan with elemental sulfur in the presence of a catalyst wherein said catalyst is prepared by heating a mixture comprising a base and an alkoxylated compound selected from the group consisting of alkoxylated alcohol, alkoxylated mercaptan, and mixtures thereof.

DETAILED DESCRIPTION OF THE INVENTION

The base useful as a component of the present invention can be an organic or an inorganic base, or mixtures thereof. Suitable organic bases include, but are not limited to tetramethylammonium hydroxide, tetraethylammonium hydroxide, tetrapropylammonium hydroxide, tetramethylammonium bisulfide, tetraethylammonium bisulfide, and mixtures of any two or more thereof. Suitable inorganic bases include, but are not limited to, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, RONa, RSNa, and mixtures of any two or more thereof; where R is a $C_1$-$C_{18}$ alkyl radical. Presently, an inorganic base is preferred because of availability and low cost of inorganic bases. Among the inorganic bases, sodium hydroxide is preferred because it is readily available and inexpensive.

The alkoxylated alcohol useful in the present invention has a general formula of $R^1O[CH_2CH(R^2)O]_nH$ where $R^1$ is a $C_1$-$C_{20}$ hydrocarbyl radical selected from the group consisting of alkyl radical, alkylaryl radical, aryl radical, cycloalkyl radical and alkenyl radical; Preferably $R^1$ is a $C_6$-$C_{18}$ alkyl radical. Most preferably $R^1$ is a $C_{10}$-$C_{16}$ alkyl radical; $R^2$ is selected from the group consisting of hydrogen, $C_1$-$C_{16}$ alkyl radicals, and $C_2$-$C_{16}$ alkenyl radicals; and n is a number of from 1 to about 20, preferably from about 2 to about 12, most preferably from 5 to 10. Generally $R^2$ can contain from 0 to about 16 carbon atoms. Preferably $R^2$ is a hydrogen or a $C_1$-$C_3$ alkyl radical. Most preferably $R^2$ is hydrogen. An example of suitable alkoxylated alcohol is TERGITOL ® 15-S-7 which is an ethoxylated alcohol, is manufactured and marketed by Union Carbide Corporation, and has the formula of $R^1O(CH_2CH_2O)_7H$ where $R^1$ is a secondary alkyl radical having 11-15 carbon atoms and 7 is an averaged number of the ethylene oxide units. Another example is an ethoxylated phenol having the same number of ethylene oxide units. Other alkoxylated alcohols are also available from Union Carbide Corporation.

The alkoxylated mercaptan useful in the present invention has a general formula of $R^1S[CH_2CH(R^2)O]_nH$ where $R^1$ and $R^2$ are the same as those described above. An example of an alkoxylated mercaptan is an ethoxylated mercaptan having the formula of $R^1S(CH_2CH_2O)_7H$ where $R^1$ is primarily a tertiary dodecyl group and 7 is an averaged number of ethylene oxide units. This ethoxylated mercaptan is a surfactant commercially available from Phillips Petroleum Company, Bartlesville, Okla. under the trade name AQUA-CLEEN® II. Another example is an ethoxylated thiophenol having the same number of ethylene oxide units. Other alkoxylated mercaptans are also available from Phillips Petroleum Company.

The weight ratio of the alkoxylated alcohol or alkoxylated mercaptan to base can vary widely, preferably from about 1:1 to about 999:1, most preferably from about 20:1 to 50:1 for best results.

The present invention composition can be made by properly mixing the components in the ratio described above employing any suitable mixing means such as shaking or stirring.

The polysulfide compound of the second embodiment of the invention has a general formula of $R^3S_qR^{4'}$ with $R^3$ and $R^4$ can be the same or different and are each hydrocarbyl radicals having about 1 to about 20 carbon atoms and are selected from the group consisting of alkyl, aryl, cycloalkyl, alkylaryl, and alkenyl radicals. Preferably $R^3$ and $R^4$ are each an alkyl radical having 3 to 15 carbon atoms. Most preferably $R^3$ and $R^4$ are each the same and are each a tertiary alkyl radical. The q is a number of 2 to about 10. Preferably q is 3.

The polysulfide can be prepared by the reaction of mercaptans and elemental sulfur catalyzed by a catalyst. The reaction is depicted as $R^3SH + R^4SH + (q-1)S \rightarrow R^3S_qR^4 + H_2S$ where $R^3$, $R^4$ and q are the same as those described above. The reaction can be carried out in any suitable reaction vessel. The choice of reaction vessel is a matter of preference to those skilled in the art.

According to the invention, the reaction of mercaptans and elemental sulfur is catalyzed by a catalyst comprising a base and an organic compound selected from the group of alkoxylated alcohol and alkoxylated mercaptan under a suitable conditions. The scopes of alkoxylated alcohol and alkoxylated mercaptan are the same as those described above.

The catalyst useful in the reaction of mercaptans and elemental sulfur can be prepared by proper mixing as described above. The catalyst also can be formed in-situ by adding a base and either an alkoxylated alcohol or an alkoxylated mercaptan before or during the contacting of mercaptans and elemental sulfur. However, it is preferably prepared by heating the mixture of the alkoxylated alcohol or alkoxylated mercaptan and the base at a temperature in the range of from about 40° C. to about 150° C., preferably from 60° C. to 100° C. for from about 10 minutes to about 5 hours, preferably from 30 minutes to 2 hours. The heating is preferably carried out under an inert gas such as nitrogen and can be under any pressure, preferably under about 1 atmosphere to about 2 atmospheres.

The suitable conditions for the contacting of mercaptans with elemental sulfur include a temperature in the range of from about 20° C. to about 250° C., preferably from 50° C. to 150° C. and a time of from about 10 minutes to about 10 hours, preferably 30 minutes to 5 hours. The pressure can vary widely from about 1 atmosphere to about 30 atmospheres, preferably from about 1 atmosphere to about 3 atmospheres.

Generally, one of the reactants, either the mercaptan or sulfur, is slowly added to the other reactant in the presence of the catalyst described above. The sulfur, upon addition, readily dissolves in the solution. Mixing of the solution and/or operating at higher than ambient temperatures will enhance the reaction rate. The amount of sulfur added depends on the desired sulfur content of the polysulfide product. For an average sulfur content of n-sulfurs per polysulfide molecule, (q−1) moles of sulfur must be added per 2 moles of mercaptan and 1 mole of hydrogen sulfide will be released per 2 moles of mercaptans reacted. The weight of the catalyst as a percentage of the weight of mercaptans is generally in the range of from 0.01 to 10%, preferably about 0.1 to 3%, and most preferably 0.5 to 2%.

Following completion of the reaction, residual hydrogen sulfide are generally removed from the crude polysulfide product by either an inert gas purge or by vacuum stripping. When using an inert gas purge, the preferable gases are nitrogen and air.

Following the removal of most residual hydrogen sulfide, the crude polysulfide product can be contacted with an alkylene oxide to further stabilize the polysulfide. Optionally, one of the bases described above can also be added to the alkylene oxide as a catalyst. The alkylene oxide can have 1 to about 10 carbon atoms. The presently preferred alkylene oxide has 1 to 4 carbon atoms and is selected from the group consisting of ethylene oxide, propylene oxide, 1,2-butylene oxide, isobutylene oxide, and mixtures thereof.

The optional basic catalyst can be employed as it is, supported on a solid support such as all forms of alumina and silica, or an aqueous solution. The presently preferred basic catalyst is selected from the group consisting of LiOH, NaOH, KOH, $Ca(OH)_2$, $Mg(OH)_2$, $Na_2O$, MgO, CaO, $NaHCO_3$, $Na_2CO_3$, $CaCO_3$, calcium phenoxide, barium phenoxide, tetramethylammonium hydroxide, tetraethylammonium hydroxide, tetrapropylammonium hydroxide, RONa, RSNa, and mixtures thereof, where R is a $C_1-C_{18}$ alkyl radical. The presently most preferred base is NaOH because of its availability and low cost.

A solvent also optionally can be used in the alkylene oxide treatment of polysulfides. The solvent generally is substantially miscible with the basic catalyst employed. It can be an ether, an alcohol or water. Suitable solvents include methanol, ethanol, propanol, tetrahydrofuran, water, and other similar oxygen-containing solvents. Methanol is the presently preferred solvent because of its combined solubilization properties, high vapor pressure, and lower density thus providing a greater density contrast between the alcohol-phase and the polysulfide phase, thereby simplifying the phase separation.

The molar ratio of the alkylene oxide to the polysulfide is from about 0.001:1 to about 50:1, preferably from about 0.005:1 to about 2:1, and most preferably from 0.01:1 to 1:1. The molar ratio of the basic catalyst, if present, to the polysulfide ranges from about 0.001:1 to about 2:1, preferably from about 0.005:1 to about 1:1, and most preferably from 0.01:1 to 0.1:1. The molar ratio of the solvent, if employed, to the polysulfide is from about 0.001:1 to about 20:1, preferably from about 0.01:1 to about 10:1, and most preferably from 0.02:1 to 1:1.

Though the basic catalyst is generally added to the crude polysulfide first, the order of adding the alkylene oxide and basic catalyst generally does not significantly affect the purity and stability of the final product. Generally, following the addition of the basic catalyst to the crude polysulfide, the mixture is mixed by a suitable means such as stirring and heated to about 50°–150° C., preferably about 60°–100° C., most preferably 65°–80° C., followed by the addition of alkylene oxide. The heating step can also be carried out after the alkylene oxide is added to the mixture.

The mixture is then further heated at the same temperature range described above for about 10 minutes to about 10 hours, preferably about 30 minutes to about 5 hours, most preferably 1 hour to 3 hours. Upon completion of heating, nitrogen sparge into the mixture can be initiated at about 1 to about 10 standard cubic feet per hour for about 10 minutes to about 5 hours.

The heated mixture can be further purified if necessary. This is usually done by conventional separation means such as filtration to remove any impurities or by distillation.

The process of the invention can also be carried out continuously. For example, the contacting of mercaptans with elemental sulfur in the presence of the invention catalyst can be done by employing continuous stir tank reactors connected in series, packed columns or towers in which the invention catalyst is supported on a solid support, and other continuous flows that are readily within the realm of one skilled in the art.

The following examples are provided to further illustrate the practice of the invention and are not intended to limit the scope of the invention of the claims.

EXAMPLE I

This example illustrates the preparation of the invention catalysts.

a) Ethoxylated Alcohol and NaOH

To a 200 ml flask equipped with thermowell, magnetic stirring bar, and condenser with $N_2$ inlet on top, was added 97.0 g of ethoxylated alcohol (Union Carbide TERGITOL ® 15-5-7) and 3.0 g of NaOH pellets. The mixture under $N_2$ was heated at 80° C. with stirring for 1 hour. The liquid was clear and reddish orange after heating. After cooling, the flask was stoppered. Avoid exposure to air as much as possible.

The catalyst was also prepared the same way as described above except that 97.0 g of the ethoxylated alcohol and 6.0 g of 50% aqueous NaOH were used.

b) Ethoxylated Mercaptan and NaOH

The catalyst was prepared the same way as above except 97.0 g unoxidized AQUA-CLEEN ® II (ethoxylated t-dodecyl mercaptan with average of 7 ethylene oxide units, available from Phillips Petroleum Company) and 3.0 g of NaOH pellets were used. After heating, the liquid was clear brown.

EXAMPLE II

This example illustrates the preparation of di-t-dodecyl trisulfide using catalyst made from an ethoxylate alcohol and sodium hydroxide.

To a 500 ml, 3-necked flask equipped with thermowell, magnetic stirring bar, and condenser with $N_2$ inlet on top was added 202.4 g (1.00 mole) of t-dodecyl mercaptan and 1.4 g of the catalyst made from ethoxylated alcohol and NaOH pellets. Under a $N_2$ atmosphere, the mixture was heated to 75° C. Then 32.2 g (1.00 mole) of elemental sulfur was added in portions over 30 minutes at 75° C. with stirring. Hydrogen sulfide was evolved and was sent to the low pressure flare. After the sulfur addition was complete, the mixture was heated to 135° C. and maintained at this temperature with stirring for 3 hours. Then the reaction mixture was sparged with $N_2$ for 2 hours at 135° C. with stirring. Sparging was stopped and the mixture cooled to 72° C. The condenser was replaced with a Dewar condenser containing ice. Propylene oxide (4.15 g, 5.0 ml) was added over 15 minutes at 72° C. The mixture was heated with stirring for an additional 2.25 hours at 75° C. Then the mixture was sparged with $N_2$ for 1.5 hours at 72° C. After cooling, the mixture was filtered to give 218 g (100.3%) of di-t-dodecyl trisulfide as a clear golden yellow liquid. Physical properties are given in Table I. The ethoxylated alcohol catalyst became part of the product so the yield as >100%.

In two other runs, 1.5 and 2.0 g of catalyst were used instead of 1.4 g. The results were the same as above with the products having a golden yellow color. Physical properties are given in Table I.

Yet in another run, 1.7 g of catalyst which was prepared from 97.0 g of ethoxylated alcohol and 6.0 g of 50% aqueous NaOH (Example I) was used. Otherwise the procedure was the same. Again, good product (Table I) was obtained.

EXAMPLE III

This example shows the preparation of di-t-dodecyl trisulfide using catalyst made from ethoxylated alcohol and sodium hydroxide in a larger scale run using 1.6 g catalyst per mole t-dodecyl mercaptan. The procedure was the same as that described in Example I except the scale was greater. The amounts of reagents were 1052.5 g (5.2 mole) of t-dodecyl mercaptan, 8.3 g of the catalyst made from the ethoxylated alcohol and NaOH pellet, and 166.7 g (5.2 mole) of elemental sulfur. All reaction times were the same as above except that the first $N_2$ sparging (at 135° C.) was 2.5 hours rather than 2.0 hours. In the propylene oxide treatment, 21.6 g or 26 mls of propylene oxide was used. Di-t-dodecyl trisulfide was obtained as a clear yellow liquid (1138 g, 100.7% yield). Physical properties are given in Table I. The ethoxylated alcohol catalyst became part of the product, so the yield was greater than 100%.

EXAMPLE IV

This example illustrates the preparation of di-t-dodecyl trisulfide using catalyst made from ethoxylated mercaptan and sodium hydroxide.

The procedure was exactly the same as the first procedure given in Example II except 2.6 g of catalyst made from ethoxylated mercaptan and NaOH pellet was used. The final product (218 g, 100.3% yield) was a clear yellow-orange liquid. Physical properties are given in Table I.

TABLE I

Physical Properties of Di-t-dodecyl Trisulfide

| Catalyst Used[a] (grams catalyst per mole mercaptan) | Appearance | Color by ATM D-1500 | Mercaptan Sulfur (ppm) | Viscosity at 40° C. (cSt) |
|---|---|---|---|---|
| Ethoxylated Alcohol and NaOH (1.4 g) | clear, golden yellow | 1.3 | 41 | 46.0 |
| Ethoxylated Alcohol and NaOH (1.5 G) | clear, golden yellow | 1.3 1.3 | 45 31 | 48.8 45.8 |
| Ethoxylated alcohol and NaOH (1.6 G) | clear, yellow | 1.3 | 41 | — |
| Ethoxylated alcohol and NaOH (1.7 g) | clear, golden yellow | 1.3 | 33 | — |
| Ethoxylated alcohol and NaOH (2.0 g) | clear, golden yellow | 1.3 | 30 | 45.1 |
| Ethoxylated mercaptan and NaOH (2.6 g) | clear, golden yellow or yellow-orange | 1.5 | 35 | 42.1 |

[a]In all runs catalysts were prepared from ethoxylated alcohol, or mercaptan, and NaOH pellets except for run using 1.7 g catalyst where 50% aqueous NaOH and ethoxylated alcohol were used.
[b]Mercaptan sulfur by weight was measured after propylene oxide treatment by pentiometric titration using mercuric perchlorate. The initial mercaptan sulfur content before propylene oxide treatment was about 3870 ppm.

The above examples show that use of these catalysts (1.4–2.6 g per mole mercaptan) gave a trisulfide product with a mercaptan sulfur content of 3870 ppm which was still too high since it caused the product to have too much odor and to be unstable (turned cloudy). However, the mercaptan sulfur content was low enough that propylene oxide could be used to reduce the mercaptan sulfur to 30–40 ppm. It was only necessary to add a small amount of propylene oxide to the reaction mixture at the end of the reaction to obtain the desired effect. Excess propylene oxide was removed by $N_2$ sparging. The colors of the trisulfide products were yellow or yellow with slight orange. Measurement of the color by ASTM method D-1500 gave values of 1.3. Use of too much catalyst in the process caused the trisulfide to be darker (orange).

It should be noted that less catalyst was required when using the catalyst made from the ethoxylated alcohol than when using the catalyst from the ethoxylated mercaptan. The first required only 1.4–1.6 g catalyst per mole of t-dodecyl mercaptan (200 g) while the second required 2.6 g per mole of mercaptan. For both catalysts, if less than these amounts were used, the final products were unacceptable. The mercaptan sulfur levels were too high, and the products were cloudy.

At the end of the reaction (after propylene oxide treatment), the trisulfide was filtered, but this removed only traces of material (negligible amount). This means that the catalyst was retained in the final product. A separate experiment also showed that the catalyst was perfectly soluble in the product. The amount of ethoxylated alcohol or mercaptan in the final product was 0.64–1.18%. An advantage of the ethoxylated alcohol over the ethoxylated mercaptan was that less (0.64–0.73%) catalyst was present in the final product.

The results shown in the above examples clearly demonstrate that the present invention is well adapted to carry out the objects and attain the ends and advantages mentioned was well as those inherent therein. While modifications may be made by those skilled in the art, such modifications are encompassed within the spirit of the present invention as defined by the disclosure and the claims.

That which is claimed is:

1. A composition comprising a base selected from the group consisting of organic base, inorganic base, and mixtures thereof and an alkoxylated compound selected from the group consisting of alkoxylated alcohol, alkoxylated mercaptan and mixtures thereof.

2. A composition according to claim 1 wherein said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, barium phenoxide, calcium phenoxide, RONa, RSNa, and mixtures thereof.

3. A composition according to claim 1 wherein said base is sodium hydroxide.

4. A composition according to claim 1 wherein said alkoxylated alcohol has a general formula of $R^1O[CH_2CH(R^2)O]_nH$ wherein $R^1$ is a hydrocarbyl radical selected from the group consisting of alkyl radical, alkylaryl radical, aryl radical, cycloalkyl radical and alkenyl radical; $R^2$ is selected from the group consisting of hydrogen, $C_1$–$C_{16}$ alkyl radical, and $C_2$–$C_{16}$ alkenyl radical; and n is a number of 1 to about 20.

5. A composition according to claim 4 wherein $R^1$ is a $C_6$–$C_{18}$ alkyl radical, $R^2$ is selected from the group consisting of hydrogen and a $C_1$–$C_3$ alkyl radical, and n is from about 2 to about 12.

6. A composition according to claim 5 wherein $R^1$ is a $C_{10}$–$C_{16}$ alkyl radical, $R^2$ is hydrogen and n is from 5 to 10.

7. A composition according to claim 6 wherein said alkoxylated alcohol is TERGITOL ® 15-S-7 which is an ethoxylated alcohol surfactant and has the formula of $R^1O(CH_2CH_2O)_7H$, wherein $R^1$ is a secondary alkyl radical having 11 to 15 carbon atoms.

8. A composition according to claim 1 wherein said alkoxylated mercaptan has a general formula of $R^1S[CH_2CH(R^2)O]_nH$ wherein $R^1$ is a hydrocarbyl radical selected from the group consisting of alkyl radical, alkenyl radical, alkylaryl radical, aryl radical and cycloalkyl radical; $R^2$ is selected from the group consisting of hydrogen, $C_1$–$C_{16}$ alkyl radical, and $C_2$–$C_{16}$ alkenyl radical; and n is a number of from 1 to about 20.

9. A composition according to claim 8 wherein $R^1$ is a $C_6$–$C_{18}$ alkyl radical, $R^2$ is selected from the group consisting of hydrogen and a $C_1$–$C_3$ alkyl radical, and n is from about 2 to about 12.

10. A composition according to claim 9 wherein $R^1$ is a $C_{10}$–$C_{16}$ alkyl radical, $R^2$ is hydrogen and n is from 5 to 10.

11. A composition according to claim 10 wherein said alkoxylated mercaptan is AQUA-CLEEN® II which is an ethoxylated mercaptan surfactant having the formula of $R^1S(CH_2CH_2O)_7H$, wherein $R^1$ is mainly a tertiary dodecyl radical.

12. A composition according to claim 1 wherein said composition is heated.

13. A composition according to claim 12 wherein said composition comprising sodium hydroxide and TERGITOL® 15-S-7 which is an ethoxylated alcohol surfactant and has the formula of $R^1O(CH_2CH_2O)_7H$ wherein $R^1$ is a secondary alkyl radical having 11–15 carbon atoms.

14. A composition according to claim 12 wherein said composition comprising sodium hydroxide and AQUA-CLEEN® II which is an ethoxylated mercaptan surfactant having the formula of $R^1S(CH_2CH_2O)_7H$ wherein $R^1$ is mainly a tertiary dodecyl radical.

* * * * *